(12) United States Patent
Colton et al.

(10) Patent No.: US 9,254,376 B2
(45) Date of Patent: Feb. 9, 2016

(54) WIRELESS TATTOO APPLICATOR

(71) Applicants: Brett Colton, Leeman (AU); Bertho Boman, Fort Lauderdale, FL (US)

(72) Inventors: Brett Colton, Leeman (AU); Bertho Boman, Fort Lauderdale, FL (US)

( * ) Notice: Subject to any disclaimer, the term of this patent is extended or adjusted under 35 U.S.C. 154(b) by 219 days.

(21) Appl. No.: 13/692,399

(22) Filed: Dec. 3, 2012

(65) Prior Publication Data
US 2013/0096599 A1 Apr. 18, 2013

Related U.S. Application Data

(63) Continuation of application No. 12/130,282, filed on May 30, 2008, now abandoned.

(51) Int. Cl.
*A61B 17/34* (2006.01)
*A61M 37/00* (2006.01)

(52) U.S. Cl.
CPC .................. *A61M 37/0076* (2013.01)

(58) Field of Classification Search
CPC ................. A61M 37/0076; A61M 37/0084; A61B 17/34; A61B 17/205; A01K 11/005
USPC .................. 81/9.22; 606/167, 169, 177–179, 606/184–186
See application file for complete search history.

(56) References Cited

U.S. PATENT DOCUMENTS 6,550,356 B1 * 4/2003 Underwood ................... 81/9.22

* cited by examiner

*Primary Examiner* — Ashley Fishback
(74) *Attorney, Agent, or Firm* — Maier & Maier, PLLC

(57) ABSTRACT

A wireless, battery powered tattooing apparatus employing a stable voltage regulator to provide stable control of the operation of the tattoo applicator. A user interface enables an artist to select a desired reciprocation frequency for the needle movement of the tattoo applicator. The selected setting is used to generate a particular voltage from the voltage regulator that in turn, controls the frequency of the needle reciprocations. A wireless receiver receives operational commands to control the tattoo applicator from a remote transmitter thereby keeping the artist's hands free to work.

11 Claims, 7 Drawing Sheets

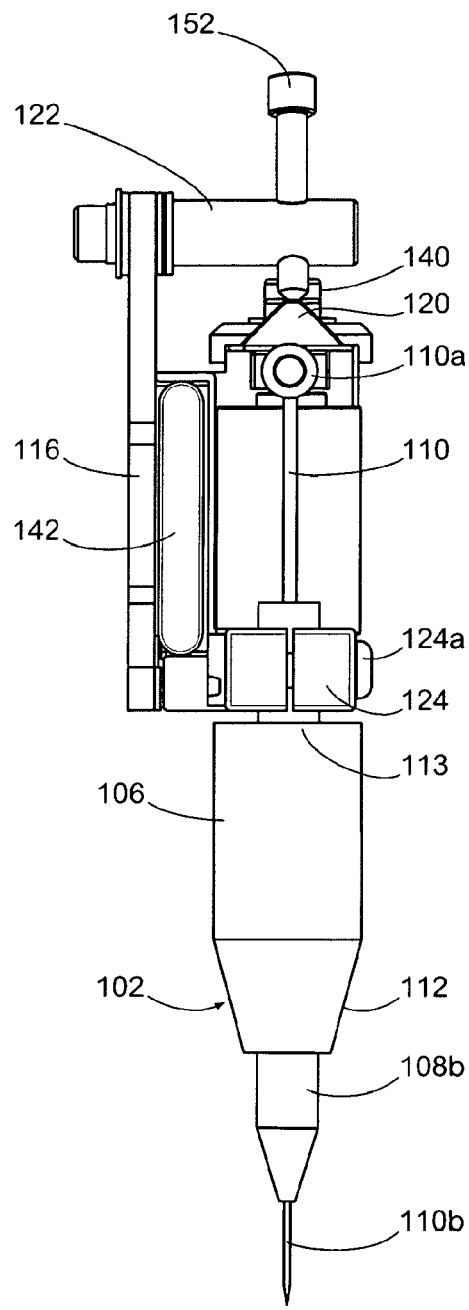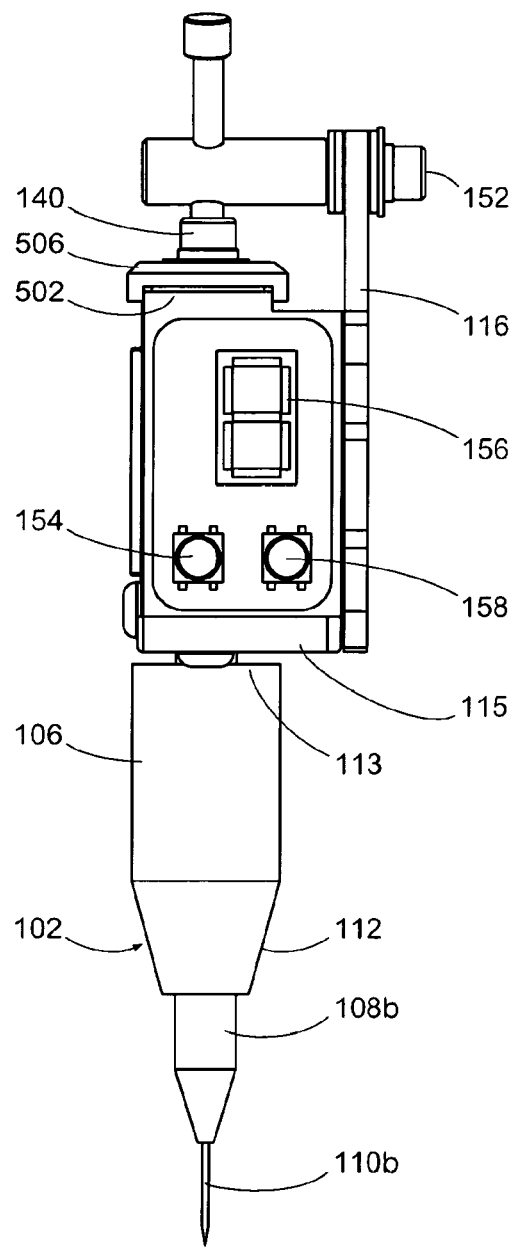
FIG. 4A    FIG. 4B

WIRELESS TATTOO APPLICATOR

CROSS-REFERENCE TO RELATED APPLICATIONS

This application is a continuation of prior application Ser. No. 12/130,282, filed May 30, 2008, which claims the benefit of the filing date of U. S. Provisional Application for Patent filed on Jun. 1, 2007, assigned Ser. No. 60/932,821 and having a title of WIRELESS TATTOOING SYSTEMS AND METHODS. These prior applications are incorporated herein by reference.

BACKGROUND

Ascertaining the exact historical beginnings of a concept such as body tattoos is a difficult task at best but, research has clearly shown that it is certainly not a recent phenomenon. Some believe that the word tattoo is derived from combining the Polynesian word "TA" which means to strike something with the Tahitian word "TATAU" which means to mark something. The existence of tattoos has been determined to be at least five thousand years old. This belief was based on the 1991 discovery of a frozen body on a European mountain. The frozen body bore a total of 57 tattoos. Today, tattoos are included in the broad spectrum of body art. Body tattoos have considerable range from a small flower, initial, etc. to a full-body themed tattoo such as Tom Leppard whose entire body is covered with leopard spots.

Whatever is the tattoo of choice, it is clear tattoos are art. The typical tattoo bearer makes a statement about himself or herself through the tattoo, whether it is politically motivated, love motivated, vanity motivated or simply an affectionate attachment to the object or style of the tattoo. Likewise, the person applying the tattoo is certainly referred to as a tattoo artist.

As is typical with most artists, the tattoo artist uses a set of tools or objects to create art where there once was none. In the tattoo arena, the primary took that is utilized by the tattoo artist is the tattoo gun. The tattoo gun in the hand of a tattoo artist is similar to the brush in the hand of a painter or a piece of charcoal in the hand of a drawer. As such, the touch and feel of the tattoo gun becomes important to the tattoo artist and in essence becomes an extension of their artistic being. Thus, it is not surprising that in general, most available tattoo guns or applicators have a similar look and feel to them. It is a design that has become popular and accepted in the industry.

In the forming of a tattoo on skin, one or more needles carrying a small quantity of ink is utilized. The needle penetrates the skin leaving a small spot of the ink which will result in the production of the discoloration of the skin. Repeating this procedure numerous times in a particular pattern with one or more ink colors of ink will result in the production of a desired tattoo.

In the creation of most tattoos, it is required to insert a needle into the skin hundreds of times, and in some tattoos, even thousands of times. A common technique of producing a tattoo is to manually insert and withdraw a needle each and every time. In order to decrease the amount of time it takes to make a tattoo, in the past it has been known to use some kind of a mechanism that causes the needle to oscillate rapidly with the user only being required to carefully move the needle from one location to another. These locations are generally adjacent to each other, and the needle will be moved continually from these locations until the desired pattern of the tattoo is reproduced. In the past, this type of mechanism has been operated with a plugged in power source.

A very important feature of modern day tattoo guns is maintaining consistent oscillations of the needle(s). For instance, when an artist is drawing the lines or outlining the tattoo, the needle(s) oscillate at a first frequency. However, when the artist is shading in areas of the tattoo, the needles generally oscillate at a slower speed. In addition, in many circumstances the depth or range of needle motion is varied. For instance, the range can be modified to penetrate deeper into the skin for leathery or darker skins, and less deep for soft pale skins. In addition, certain looks can be achieved by varying the depth of the ink penetration. Thus, maintaining the oscillation frequency as well as the motion range of the oscillation is important to the artist to enable consistency in the application of the ink and control. In the past, the oscillation frequency has been provided by using a stabilized voltage source that is fed to the tattoo gun from an external voltage supply through one or more wires.

The current generation of tattoo machines is moving towards a wireless or non-connected type of arrangement. However, the typical wireless tattoo mechanisms on the market are either too unsanitary and/or have too much extra weight resulting in an artist having to o struggle while creating a tattoo or experiencing fatigue. There are numerous problems with existing wireless tattoo applicators. For instance, employing inefficient voltage conversion technology has resulted in using oversized batteries and hence, resulting in too much extra weight in the tattoo gun. In addition, the lack of universal compatibility has resulted in creating a sanitation issue in that a voltage controller which is used with a possibly infected glove may be used numerous times throughout the process of a tattoo. Another issue that is present in the state of the art is wireless interference that can effect the operation of the wireless tattoo applicator. Yet another issue relates to the inconsistency of power and/or frequency used to control the tattoo gun. Even further, the input voltage of the tattoo applicator can be influenced by the external power supply and is therefore unreliable.

Thus, there is a need in the art for a wireless or cordless tattoo mechanism that can improve the usability of the device from the artists' perspective, as well as provide a sanitary environment for both the artist and the customer.

BRIEF SUMMARY

The present invention is directed towards various aspects, features and embodiments of a wireless tattoo applicator. In general, an exemplary embodiment of the present invention is a wireless, cordless or non-tethered tattooing apparatus that employs the use of batteries and a stable voltage regulator to provide a stable control of the operation of the tattoo applicator. More specifically, one embodiment includes a user interface that enables an artist to set a desired reciprocation frequency for the needle movement of the tattoo applicator. The selected setting is used to generate a particular voltage from the voltage regulator that in turn, controls the frequency of the needle reciprocations. In another embodiment of the invention, the tattoo applicator includes a wireless receiver through which it can receive operational commands. A remote transmitter can then send operational commands to the wireless tattoo applicator to control the operation of the applicator. For instance, a foot pedal may be used to trigger the transmission of an on or off signal. The reception of these commands will result in either turning the reciprocating action of the tattoo applicator on or off. Similarly, a remote device may be used to select the reciprocating frequency. A command indicative of the selected frequency and then be transmitted to the tattoo applicator and the applicator can adjust its settings accordingly.

Various techniques are employed in embodiments of the present invention to help reduce battery consumption and thereby increase the charge life of the batteries running the tattoo applicator. One technique employs a synchronization protocol that periodically transmits an on command to the tattoo applicator until the artist actuates a switch to have an off command sent. Further, such an embodiment includes a software algorithm or module that continuously looks for the on command and then resets a watchdog timer when the on command is received. If the on command is not received in a desired time period, the tattoo applicator can automatically power down. This aspect of the invention advantageously reduces power consumption and also decreases power interrupts due to false power off requests.

Another technique that can be employed is the application of intelligence in the control of the electromagnetic circuitry used to creating the reciprocating motion of the armature. For instance, rather then triggering the application of current or excitement of the coils based on the armature closing the contacts with the circuit, embodiments of the present invention can capitalize on pendulum motion technology to reduce the energy required to move the armature. For instance, typical tattoo applicators begin to provide power to move the armature downward too early in the pendulum swing. In embodiments incorporating this aspect of the invention, an algorithm is used to more accurately assess when the armature has crested the end of a swing and momentum is starting in the other direction. At this point, power is applied to assist in the motion.

In addition, embodiments of the invention may employ the use of a spring to help absorb energy during the down swing of the armature and release this energy back in the up swing of the armature. Advantageously, this aspect of the present invention operates to reduce power consumption and prolongs the life of the tattoo applicator by reducing mechanical stress.

These and other aspects, features and embodiments of the present invention are more fully described in the detailed description and illustrated in the figures.

BRIEF DESCRIPTION OF THE SEVERAL VIEWS OF THE DRAWING

FIG. 4A is a front view elevation of the embodiment illustrated in FIG. 1.

FIG. 4B is a back view elevation of the embodiment illustrated in FIG. 1.

DETAILED DESCRIPTION OF EMBODIMENTS OF THE INVENTION

Figure 1:
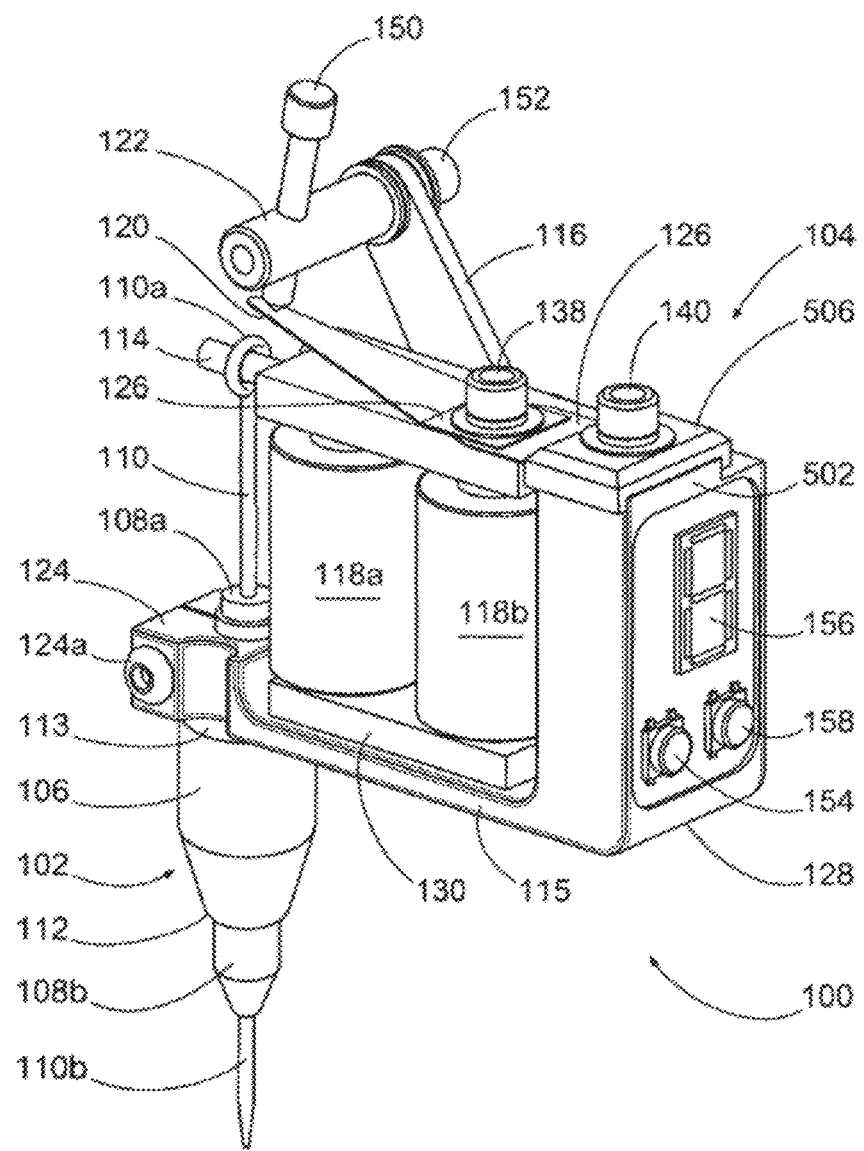
FIG. 1 is a perspective view of a tattoo gun incorporating various features and aspects of the present invention.

The present invention, as well as features and aspects thereof, is directed towards providing a wireless, cordless or non-tethered tattoo applicator or gun for use in the application of tattoos. More specifically, an embodiment of the present invention includes a battery powered tattoo gun that includes a stable voltage regulator that is used to control the oscillating or reciprocating frequency of the needle assembly and that can be set at various settings for differing frequencies. Another embodiment of the invention is a wireless and battery operated pen tube drive assembly that can receive a plurality of brands and styles of tattoo gun pen tubes and control the application of ink by driving the needle assembly of the pen tubes in a stable manner. One inventive aspect that can be incorporated into various embodiments of the present invention is a power saving technique that saves power by cooperatively working with the mechanical momentum of the device to save battery drainage. Another inventive aspect that can be incorporated into various embodiments of the present invention is a redundant protocol that operates to power down the tattoo gun when it is not in use but, that also alleviates the risk of false shut-offs during operation.

To maintain freedom of movement and availability of hands, an embodiment of the wireless tattoo gun may exclude a power on/off switch on the tattoo gun and instead, utilize a wireless transmitter to send on and off signals to the wireless tattoo gun. Advantageously, this aspect of the present invention allows the wireless tattoo gun to be powered down during non-use to help conserve power, to free-up the artists' hand from having to turn the gun on and off, and for safety and sanitation purposes. For instance, in one embodiment of the invention a foot pedal may be used to turn the wireless tattoo gun on and off. The foot pedal can toggle an on/off switch which either activates or deactivates a constant IR or RF signal. The foot pedal can be either directly connected to a base unit (e.g., a base unit comprising a transmitter and/or battery charger) via a wire plugged into a jack, directly integrated into the base unit or wireless (such as IR or RF). Alternatively, the foot pedal can be a separate unit that is, for example, battery operated and sends the on or off command via an IR or RF signal using the foot pedal's own PCB and transmitter.

The wireless communication can be conducted via infrared technology or radio frequency technology. In either case, another aspect of the present invention is a synchronization technique and redundancy techniques to alleviate interference between a wireless tattoo gun and other wireless tattoo guns or other transmitting devices.

Another inventive aspect of the various embodiments of the invention includes a non-rotating spring holder. In general, this aspect of the present invention helps to prevent the spring from being rotated during adjustments and thereby causing alignment problems.

These and other aspects, features and embodiments of the present invention will be more clearly understood in view of the following figures and the descriptions associated therewith in which like labels represent like elements throughout the several views.

Figure 2:
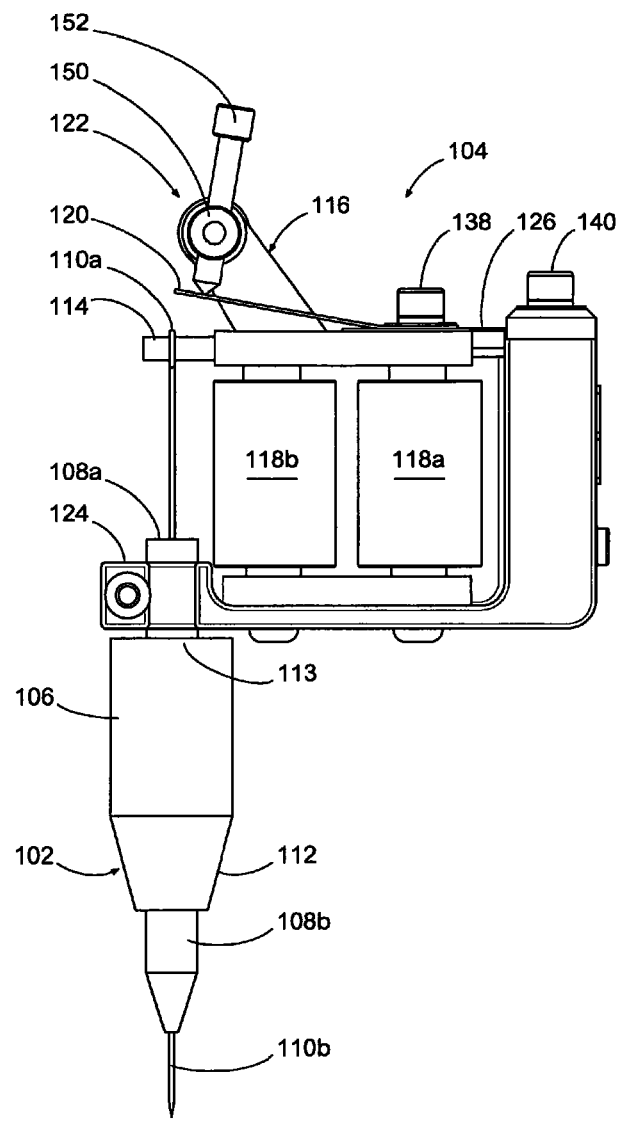
FIG. 2 is a side view elevation of the embodiment illustrated in FIG. 1.
Figure 3:
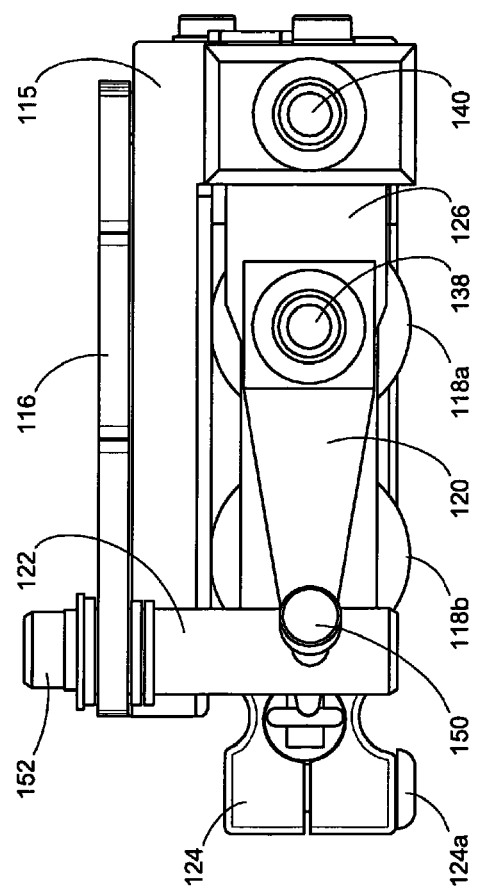
FIG. 3 is a top view elevation of the embodiment illustrated in FIG. 1.

FIG. 1 is a perspective view of a tattoo gun incorporating various features and aspects of the present invention. FIG. 2 is a side view elevation of the embodiment illustrated in FIG. 1. FIG. 3 is a top view elevation of the embodiment illustrated in FIG. 1. FIG. 4A is a front view elevation of the embodiment illustrated in FIG. 1. FIG. 4B is a front view elevation of the embodiment illustrated in FIG. 1.

Looking at FIG. 1, the tattoo gun 100 includes a pen assembly 102 and a drive assembly 104. The pen assembly 102 includes a pen tube 106, a barrel 108 and a needle assembly 110. It should be appreciated that reference numbers, such as 110 refer to a component or assembly and if a letter is appended to the reference number, it refers to a portion, feature, or aspect of the component or assembly. As such, some components or assemblies only include reference numbers with letters appended to identify or accent portions of features of a component or assembly but the description will refer to the component or assembly by simply using the reference number, even if it does not appear by itself in the figures.

In the illustrated embodiment, the pen tube 106 is shown as being cylindrically shaped over a portion of its surface and then tapering off to a blunt end 112. The artist typically holds the tattoo gun 100 by holding the pen tube 106 similar to any other writing instrument. In various embodiments the pen tube may be longer or shorter and may have a different shape (octagonal, triangular, etc) as well as contours or various surfaces to facilitate gripping, holding and comfort. The pen tube 106 includes a hollow core through which a barrel 108 extends. The pen tube 106 is shown as ending at the surface of the drive assembly 104 whereas the barrel 108 is shown as extending out of the top 113 of the pen tube 106 and into the drive assembly 104. In addition, the barrel 108 extends out of the tapered end 112 of the tube pen 106.

The barrel 108 includes a top end 108a that extends out of the top of the pen tube 106 and a tapered end 108b that extends out of the bottom of the pen tube 106. The barrel includes a hollowed out, axial radius and is tapered on the lower end. The tapered end of the barrel can receive a needle assembly 110.

The needle assembly 110 extends through the axially aligned bore of the barrel and a top end 110a of the needle assembly is coupled to an armature 114 of the drive assembly 104 and a bottom end 110b extends out of the tapered end of the barrel.

The drive assembly 104 includes a frame body 115, a frame plate 116, coils 118a and 118b, spring 120, spring tension assembly 122, armature 114, tube assembly lock assembly 124, armature spring and active plate 126, base 130, spring holder 506, circuit compartment 128, display 156 and control or interface devices 154 and 158.

The pen assembly 102 can be a completely separate item from the drive assembly 104. In the illustrated embodiment, the pen assembly 102 is coupled to the drive assembly by inserting the top end of the barrel 108a into the tube assembly lock assembly 124 and the top end of the needle assembly 110a through the bore of the barrel 108. The tube assembly lock assembly 124 is then used to secure the pen assembly 102 to the frame 116. In this illustrated embodiment this is accomplished by tightening lock assembly screw 124a but, in other embodiments clamps or pressure levers may also be used. The needle assembly 110, which may include a single needle or several needles joined together, is mounted through the bore of the barrel 108 in such a manner to allow the needle assembly 110 to freely slide within the barrel 108. The top portion of the needle assembly 110a includes an interface to the armature 114. In the illustrated embodiment, this interface includes a loop or band on the end of the needle assembly through which a narrowed end of the armature 114 can be inserted. However, it should be appreciated that the various embodiments of the present invention are constructed to accept a wide variety of pen types and can be joined to the armature 114 in a variety of manners.

The coils 118a and 118b set on or mounted to the base plate 130 which is coupled to the frame body 115. The armature 114 extends perpendicular to the coils 118 over the top of the coils. The spring 120 rests over the armature 114 and when pressure is applied to the spring via the spring tension assembly 122, a downward force is placed on the armature. The spring 120 is attached to the armature 114 via screw or connector 138 and the force from the spring tension assembly 122 and the connector 138 keep the spring 120 in place. Armature spring and active plate 126 is also connected to the armature 114 via connector 138 and to the frame body 115 via connector 140 and spring holder 506.

The circuit compartment 128 is used to house the electronics and controls for the tattoo gun 100. The specifics of the electronics and controls can vary from embodiment to embodiment and as such, the details are not described. However, in an exemplary embodiment, the electronics may include a power supply including one or more batteries 142 that are shown as being mounted under the frame plate 116 but, in other embodiments can be mounted under the frame body 115, within the electronics compartment 128 or other locations.

The electronics may also include a circuit board having a processor, a micro-controller, A/D converters, D/A converters, control outputs, sensor inputs, display drivers, a display 156, etc. The circuit board and components cooperatively provide functionality that can include an infrared receiver and/or transceiver, or an RF receiver and/or transceiver, a battery charging circuit, a display interface, a user interface including one or more buttons, dials, potentiometers or other adjustments, a stable voltage regulator circuit, a micro-controller or processor, and an interface to the coils 118 for providing or restricting a current from flowing through the coils.

One of the advantages of using a battery to supply power through the voltage regulator is the accuracy of the resulting voltage and frequency. An embodiment of a tattoo gun is configured to provide approximately a 99% likelihood that a voltage level displayed on display 156 is an accurate depiction of the voltage being applied to the control circuit and that the frequency will remain substantially even, in line with the varying voltage setting. This is a substantial improvement over a main power source where a power supply can vary up to 10% in a single day, and a consistent frequency or power can not be guaranteed.

The voltage regulator operates to provide a steady fixed voltage to the electronic circuitry even though the supply (battery) voltage is varying (i.e. is decaying over time and can fluctuate due to temperature). Because of the stable, regulated voltage the electronics perform reliably and consistently without changing the tattoo gun's speed or operating characteristics as the battery is being discharged. When the battery is too low to adequately power the circuit board or control circuits through the voltage regulator, the tattoo gun will shut down after providing a proper warning that the battery is too low to continue operation.

In one embodiment, the circuit board can be mounted to the frame body 115 of the tattoo gun 100 and can be covered by a coating film which protects the circuit board from corrosion and makes the circuit board resistant to liquids/humidity/cleaning and/or static electricity. In another embodiment, the electrical components 145 and 146 and the circuit board, as well as the entire circuit compartment 128 can be covered with a moisture and/or corrosion resistant coating to provide a greater life expectancy of the electrical components and to facilitate safe cleaning of the machine when required without the possibility of damaging the components. The coating can be substantially impervious to fluids.

The tattoo gun or applicator 100 may include an on/off switch 158 which connects/disconnects the battery(ies) 142 to/from the circuitry in the circuit compartment 128. A battery level indicator, such as a series of LED's and/or an LCD panel or a display 156 can be used show the expected remaining battery life. In addition, the display 156 can be accessed and controlled by a processing unit to display other information such as the current frequency setting, status information, etc. It should be appreciated that although a single 8-segment display is illustrated in the figures, this is simply a non-limiting example of the display. Other embodiments can include a variety of display types including multiple segment displays, LEDs, LCDs, electro-illuminescent devices, or the like.

Figure 5:
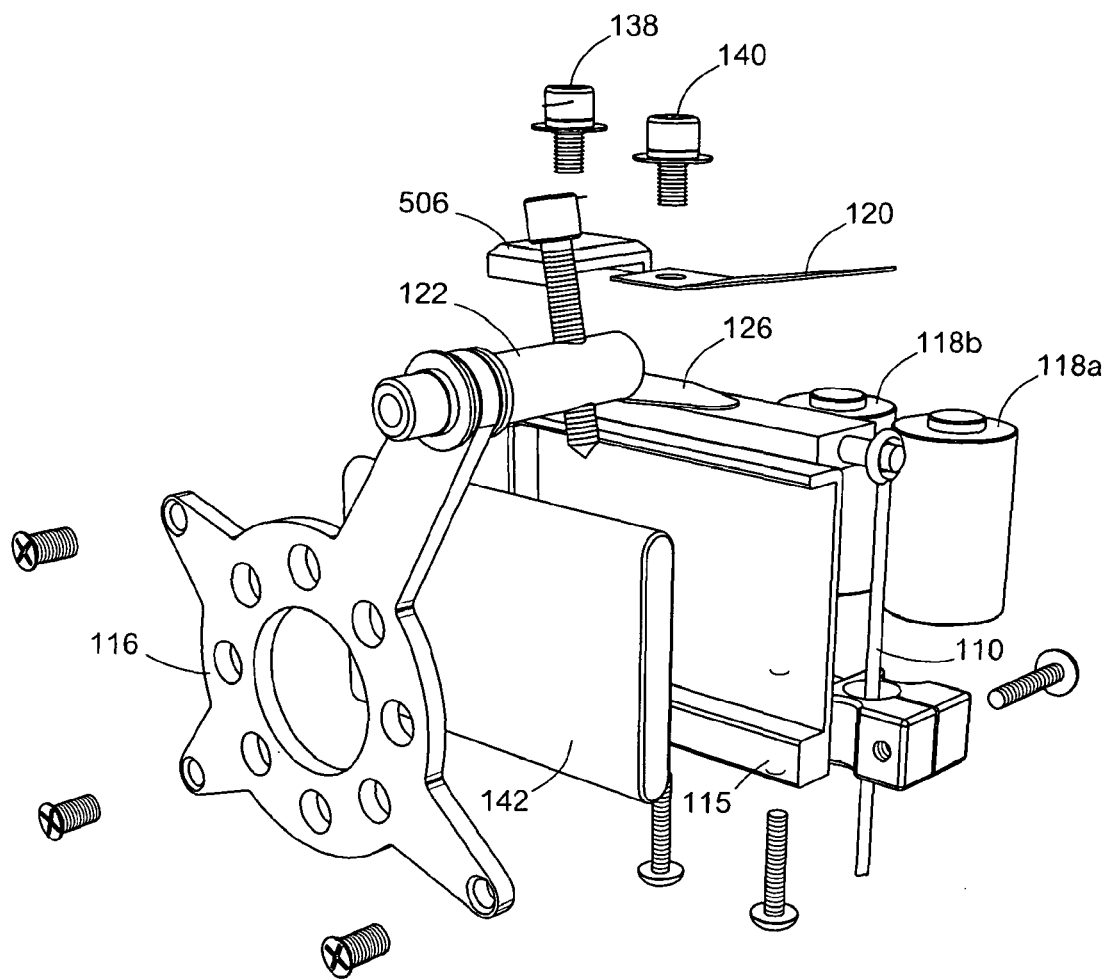
FIG. 5 is a perspective view of one embodiment of the frame 116 of the drive assembly 104.

FIG. 5 is an exploded perspective view of one embodiment of the invention that more clearly shows the frame body 115 and frame plate 116 of the drive assembly 104. One aspect that can be incorporated into various embodiments of the present invention is the use of an extra light frame body 115 and/or frame plate 116 comprising light-weight material such as for example, but not limited to metal, graphite, composites, glass fiber and/or polycarbonate materials. Using a light-weight material such as one of the aforementioned materials allows an embodiment of invention to have a similar weight as or to be lighter than the weight of a common two-coil tattoo applicator. In addition, the frame plate 116 may be easily removed and substituted with a decorative plate that allows for customized embodiments to be created. In addition, decorative face plates can be mounted to the frame plate 116 in other embodiments.

The battery 142 is shown as being mounted behind the face plate 116 and within a cavity defined by the surface of the frame body 115.

Figure 6:
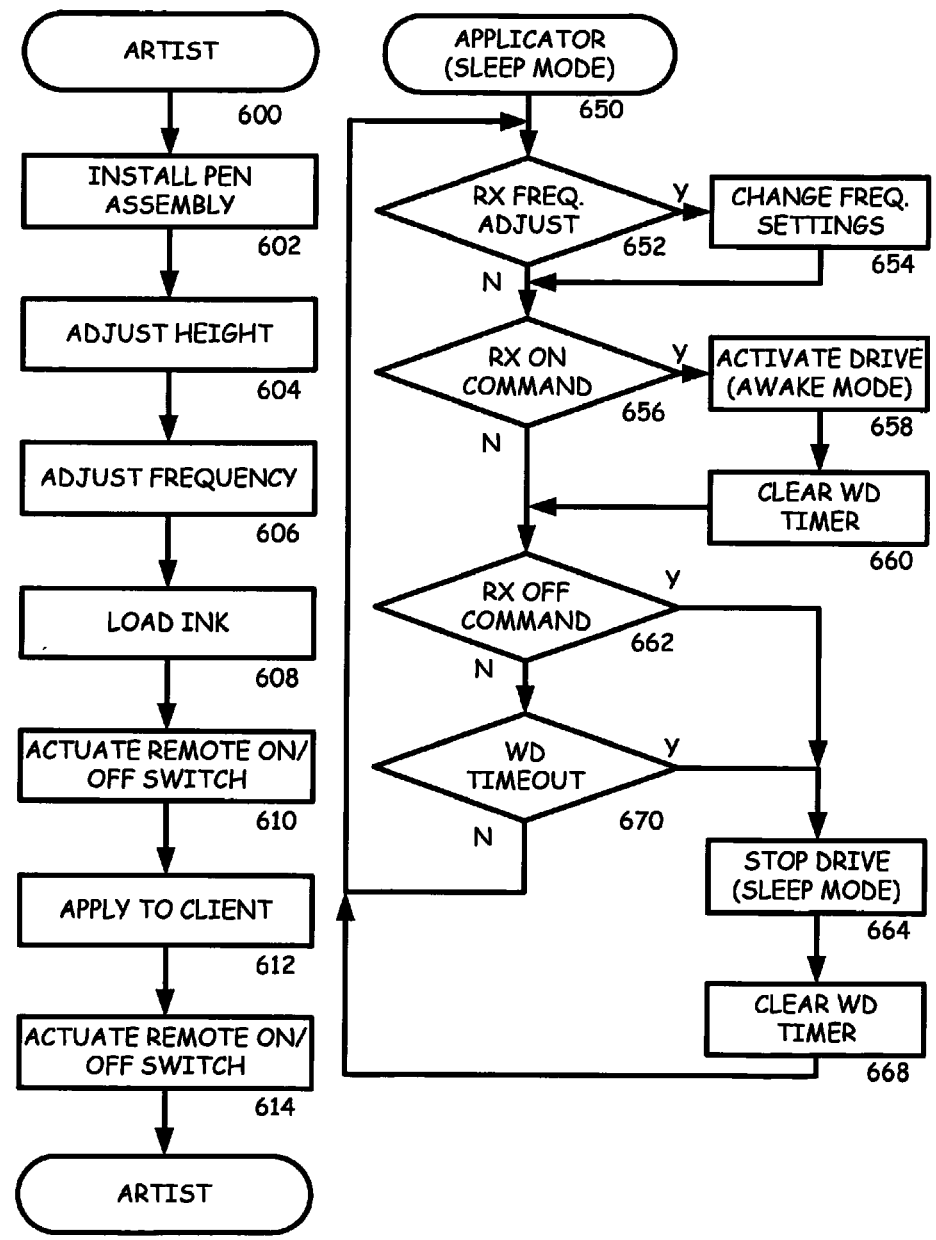
FIG. 6 is a flow diagram illustrating the operational steps of an embodiment of the present invention as described above in conjunction with FIGS. 1-5.

FIG. 6 is a flow diagram illustrating the operational steps of an embodiment of the present invention as described above in conjunction with FIGS. 1-5. The illustrated flow diagram shows the operations of an artist 600 or a user of an applicator 650, as well as the operations or steps of the applicator 650. It should be appreciated that the steps described are not all required in all embodiments and all operations of an embodiment of the invention. In addition, the steps do not necessarily have to be performed in the illustrated sequence.

Initially, the artist installs 602 the pen assembly 102 into the drive assembly 104 using the tube assembly lock assembly 124. The artist can then adjust the height 604 by adjusting the spring tension assembly 122. This is accomplished in the illustrated embodiment by actuating the coarse adjustment screw 150 or the fine adjustment screw 152 to adjust the length of the needle 110 stroke or the height or depth of the needle 110 movement. The reciprocating frequency of the needle 110 or the rate of oscillation or vibration can also be adjusted 606. This adjustment is performed in the illustrated embodiment by changing the frequency using actuator 154 that controls a voltage controller. For instance, in one embodiment actuator 154 could be a potentiometer that is used to adjust the voltage/frequency. In another embodiment, the actuator 154 may be a push button that increases or decreases a current voltage/frequency value. In other embodiments, additional actuators may be used such as pre-programmed adjustment values, increment, decrement, etc. It will be appreciated that in some embodiments, a signal that identifies a desired setting may be transmitted to the applicator rather than using the actuator 154. For instance, a remote control unit may include the ability to select a desired setting and then transmit that signal to the applicator. This could be accomplished via a dial, a roller ball, a series of switches/buttons, etc. For instance, a remote control foot pedal may include a plurality of buttons and an artist can alter the control of the applicator (such as the reciprocating frequency) by tapping on the various buttons with his or her foot. In other embodiments, the foot pedal may operate as an accelerator constantly transmitting voltage/frequency level settings based on pressure being applied to the foot pedal.

The ink can be loaded 608 for application to the client or customer. Those skilled in the art will be familiar with the various techniques for loading ink into a tattoo gun including systems in which the needles 110 are dipped into a reservoir of ink or the ink is automatically released from the pen tube or barrel. Once the applicator is set up in the manner desired by the artist and/or for the particular situation, the artist can actuate the remote on/off switch 610 to activate the applicator (change it from a sleep mode to an awake mode).

Figure 7:
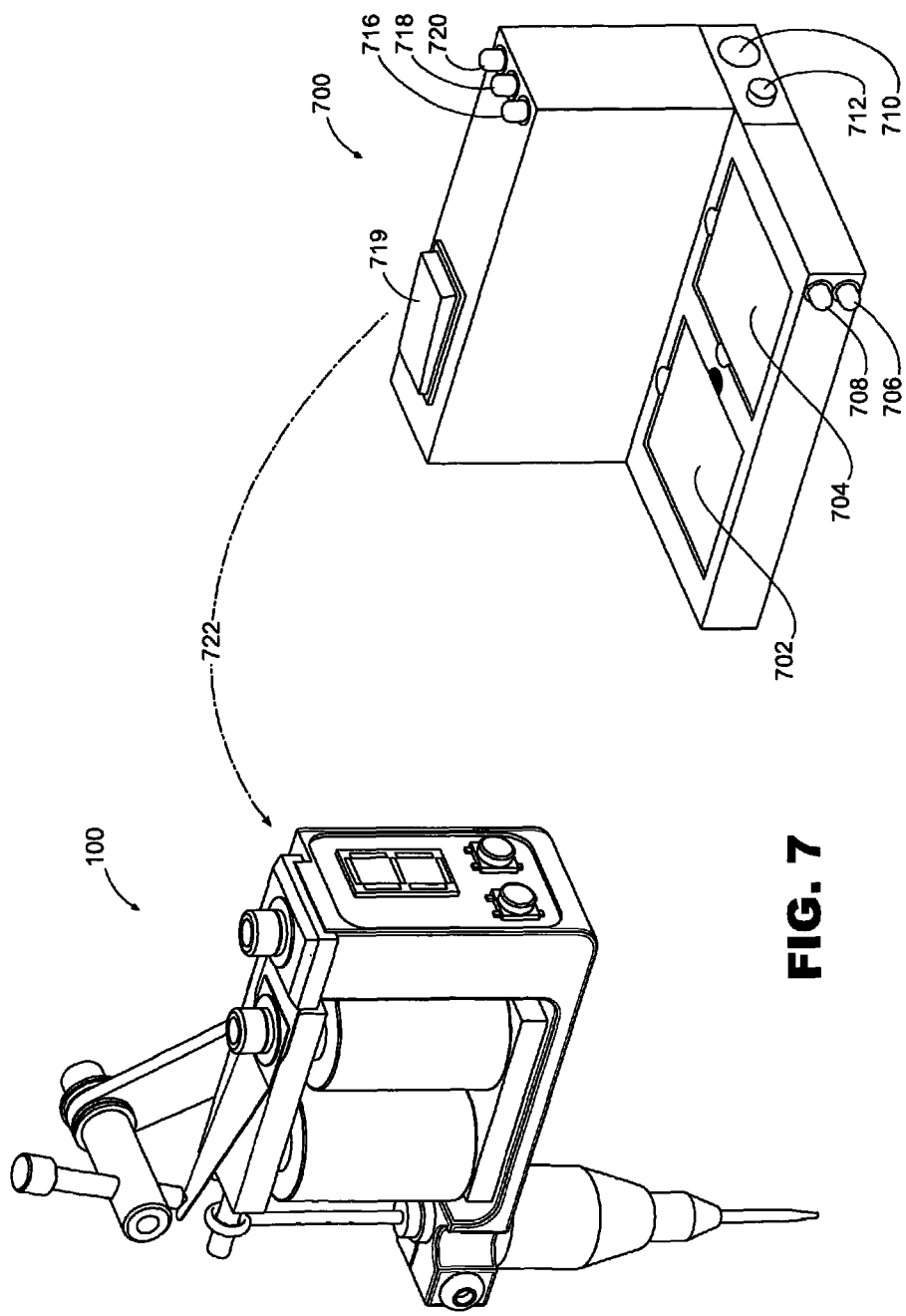
FIG. 7 is a perspective view of an exemplary battery charger and remote transmitter that can be used with various embodiments of the present invention.

FIG. 7 is a perspective view of an exemplary battery charger and remote transmitter that can be used with various embodiments of the present invention. The battery charger and remote transmitter (also referred to as a base unit or remote control) can include a frame/cover made out of metal, glass fiber and/or polycarbonate. The base unit can house a base unit PCB and/or a transmitting/battery-charging PCB. The base unit 700 includes two battery charging slots or receptacles 702 and 704 for receiving batteries to be charged and LED charge indicators 706 and 708 to indicate respectively when the batteries in slots 702 and 704 are charging and/or charged. The base unit may be configured to charge only one battery or multiple batteries at the same time.

The base unit may also include a transmitter and/or receiver for communicating with an applicator 100. The transmission technology may be any wireless technology including infrared, RF, audio, WIFI, 802.11, BlueTooth, WIMAX, etc. In one embodiment, the remote transmitter 700 simply sends commands to the applicator 100 in a single communication direction; however, other embodiments may provide two way communications. The base unit 700 includes a power connector 710 for powering the circuitry from a standard 110V or 240V source and an on switch 712 for turning on the charging circuitry and/or for turning on the base unit. On the top of the transmitter, an applicator activation switch 714 may be included along with status indicator 716, 718 and 720. In an exemplary embodiment, the step of actuating the remote on/off switch 610 would include pressing the applicator activation switch 714.

In one embodiment of the present invention, actuating the applicator activation switch 714 results in transmitting an ON command to the applicator 100 over wireless communication link 722. It should be appreciated that the remote transmitter does not necessarily have to be coupled to a battery charger. For instance, in some embodiments the transmitter may reside in a foot pedal that is positioned proximate to the operating area and as such, the artist can press the applicator activation switch 714 with his or her foot thereby keeping both hands free to hold the actuator 650 and stretch the client's skin.

An embodiment of a base unit can have one or more of the following features and/or functionalities:
a) A base unit can be configured to transmit voltage regulation/speed information to a tattoo applicator via an IR or RF signal. Alternatively a user can use a voltage regulator dial on the tattoo applicator. The voltage regulator dial can be removable from the tattoo applicator so that it can be sterilized. A base unit can be configured to either send the on signal solely, or it may—while sending the on signal, also transmit an indication of the voltage that the receiver/tattoo applicator should run at.
b) A base unit can be configured such that each time any of the corresponding tattoo applicators/receivers are placed sufficiently close to the base unit and both units are turned 'on', the base unit will synchronize with that receiver only and will not interfere with any other wireless machine in the vicinity, even if the base unit is sending a very 'long' coded signal (On+voltage) while the artist wants to use the voltage regulator on the base unit and not the one on the tattoo applicator. A base unit stays synchronized with a tattoo applicator until the base unit power supply is turned off (resetting it until turned on and synchronized again). This facilitates the ability to use any of the tattoo applicators with any of the base units without any interference between other similar units or any other wireless machinery in the vicinity. A signal transmitted by the base unit can be encoded after each transmitter is synchronized with a receiver. As a result, many machines can be operated in the same room without interference. The encoding can be formulated by a microprocessor within a base unit PCB and can be configured such that the base unit synchronizes with any one of a plurality of tattoo applicators.

c) A base unit while charging a battery can receive information from the battery's 'information' terminal. This ensures that charging will only take place when it is safe to do so, and that the charging stops when the battery is fully charged. The base unit can indicate when each battery is being charged and also indicate when the each battery is full. This can be achieved via, for example, a series of LED lights or an LCD digital panel.

Returning to FIG. 6, while operating in the sleep mode, an exemplary applicator 650 may maintain a background process running or may periodically run a quick check to see if any events have occurred. For instance, in one embodiment, the applicator 650 may execute a continuous loop that checks for frequency adjustments, command receptions and watchdog timer status. More specifically, the applicator 650 may monitor the frequency adjustment actuator 154 and or other controls to determine if an artist has modified or adjusted the frequency setting. If a frequency adjust is detected 652, the applicator 650 can change or modify the internal frequency setting 654. In addition, the applicator 650 may check to see if an ON command has been received 656 from a remote transmitter 700. If an ON command is received 656, the applicator 650 can enter an awake mode 658 and clear the watchdog (WD) timer.

Entering the awake mode involves turning on the reciprocating action of the applicator. The awake mode is entered by actuating or closing a switch that completes a circuit path. In one exemplary embodiment, circuit path allows current to flow through the base plate 130, through the coils 118 and then through the active plate 126. The current flow through the coils 118 causes the coils to become electromagnetic. The electromagnet force operates to pull down the metal armature 114. When the armature 114 is pulled down by the electromagnetic force, the needle assembly 110 descends and the electrical connection between the coils 118 and the active plate 126 is broken. As a result, the electromagnetic force is then removed and the armature 114 can spring back towards its previous position thereby retracting the needle assembly 110. Returning to its previous position once again completes the circuit path between the coils 118 and the active plate 126 and then the cycle continues to repeat. Thus, this cycle results in creating a reciprocating motion of the needle assembly.

In another exemplary embodiment, the application of the voltage to the circuit is controlled electronically. As such, rather than the mechanical action breaking the circuit and causing reciprocation, a voltage level associated with a selected frequency is applied to a circuit. Based on the voltage level, the circuit operates to turn on and off a supply voltage to the coils 118. The frequency of turning the supply voltage on and off is the reciprocating frequency of the needle assembly 110. This type of functionality can be achieved in a variety of techniques including use of a 555 timer such as those available from TEXAS INSTRUMENTS, a capacitor charging and discharging circuit, a TRIAC circuit, etc.

The applicator continues by checking to see if an OFF command has been received 662 from the remote transmitter 700. If an OFF command is received 662, the applicator 650 can re-enter the sleep mode 664 and clear the watchdog timer 668.

In an exemplary embodiment of the invention, a protocol can be employed to control the operation of the applicator 650 and thereby reduce battery consumption. For instance, in some products on the market, an infrared signal is used to turn on a device. As long as the signal is being received, the device operates. However, such a system is susceptible to temporary interrupts due to blocking of the transmission path or saturation of the signal. Similar problems may arise in an RF based solution. In an exemplary embodiment of the invention, an ON signal is transmitted to the applicator 100 to turn the applicator on or to activate the applicator. The applicator 100 then continues to operate unless an OFF command is received or until a watchdog timer timeout event occurs. As an example, the remote transmitter 700, upon detecting that the applicator activation switch 714 has been actuated, will begin periodically transmitting an ON command. Each time the applicator 650 receives an ON command, the applicator 650 clears or resets the watchdog timer. The watchdog timer is set such that if an ON signal is not received for a specified period of time (which will typically be longer than the period between transmissions of the ON command—such as 2 or 3 times), then the applicator may assume that it is out of range of the transmitter 700 and automatically stop the reciprocating action and enter into the sleep mode. In some embodiments, this action can be preceded by a warning such as a beeping or the flashing of the display 156. However, if an ON command is received, prior to the watchdog timer timing out, then the watchdog timer can be cleared or reset.

Thus, the applicator 650 can also check to see if the watchdog timer has timed out 670. If the watchdog timer has timed out, the applicator 650 can stop the reciprocating action (the drive) and re-enter the sleep mode 664. In addition, the applicator can clear the watchdog timer 668.

The applicator can continuously flow through the loop checking for frequency adjustments 652, reception of an ON command 656, reception of an OFF command 662 and a watchdog timer time out 670.

While the applicator 650 is awake and the needle assembly 110 is reciprocating, the artist can then apply ink to the client 612. When the artist needs to stop, change needle assemblies, etc, the artist can again actuate the remote on/off switch 614 to stop the reciprocation of the needle assembly 110.

Various other aspects, functions and features may also be incorporated into various embodiments of the present invention. Each of the following aspects, functions and features, although in and of themselves may be considered to be inventive elements, are not necessarily required in all or any embodiments of the present invention.

One embodiment of the present invention includes a voltage regulator that is sufficiently large so that the artist can avoid touching other parts of the applicator when adjusting the voltage regulator. For instance, a knob can be used for actuating the control 154. In other embodiments, the knob may even be removeable so that it can be sterilized.

The described embodiments of the present invention have indicated that the voltage regulator is embedded in the applicator. It will also be appreciated that the voltage regulator may be incorporated into a base unit instead. In such an embodiment, a transmission signal controlling the frequency of reciprocation can be transmitted to the applicator, received and then used to control the reciprocation of the needle assembly 110.

One advantage of the present invention is that it is universally adaptable for use with any or most pen assemblies. Typically, an artist may use 2-4 or more applicators or guns for creating a single tattoo. The various embodiments of the present invention allow the artist to easily swap out pen assemblies and needle assemblies and as such, a single gun can easily be used. However, many artist may still prefer to use multiple applicators. In a typical environment, each applicator would need to have a corresponding remote transmitter. An embodiment of the present invention incorporates technology to enable the transmitter to adapt and synchronize with as many tattoo applicators as required for an artist (one at a time). Advantageously, this feature allows the artist to control multiple applicators from a single transmitter.

More specifically, when multiple IR or RF controlled devices are used in the same area, there is the potential for the transmitted signals to interfere with each other. Such interference may result in degraded sensitivities and poor range, or one unit may inadvertently and unintentionally be controlled by the controller or control signals meant for another unit. This problem can be even more aggravated when many similar units are being operated in the same area and more or less continuously sending out IR or RF signals. Several features can be incorporated into various embodiments of the invention to prevent this and improve the reliability of the system.

One such feature is the synchronization of the transmitters. For instance, each transmitter can include a channel selector and each device can be assigned to a unique channel. These assignments can be performed at time of manufacturing or, the devices can be adjusted on site by the customer. For instance, each applicator may include one or more switches that can be used to define the control channel for the applicator. The transmitter can also includes a switch that is used to tune the transmitter to a particular channel. Thus, the transmitter can be forced to communicate on a specific channel and, the applicators will only respond to commands received on their unique channel. It should be appreciated that the channels may be physical (i.e. different frequencies) or they may be logical by including synchronization commands, encoding or signals that identify which applicator for which the signal is intended.

In another embodiment, each transmitter may include a channel selector for selecting a device channel for which only the matching receiver device will respond. In addition, each transmitter can include a receiver that monitors signals from other transmitters and adjusts its internal timing so as not to interfere with them.

In yet another embodiment, a software protocol that is independent of which unit is turned on first may be employed. Normally, there is a master unit in the system, Channel-0, that is sending out synchronizing signals for the other transmitters to lock onto and thereby to control or limit interference. However, if the master transmitting on Channel-0 is missing or not turned on, the software will automatically assign the master function to a lower level unit. If Channel-0 is subsequently turned on, it will only operate in a listening mode and in essence, will operate as a slave since there is already a reassigned master in the system.

Other embodiments of the invention, especially those that employ infrared (IR) communication, may include redundancy to improve the reliability of operation. For instance, to prevent performance degradation due to blocked IR transmissions, the remote controller may include multiple IR transmitters aimed in different directions. Similarly, the remote controller may include multiple IR receivers aimed for receiving signals from different directions to prevent performance degradation due to blocked received signals. Likewise, the applicators can include multiple IR receivers and/or transmitters for the same reasons. In addition, because IR receivers are susceptible to interference from light sources, such as the sun, a processing unit can be used to monitor the various receivers to detect if one or more of the receivers is overloaded or saturated by an external light source. Each IR receiver can be independently monitored and if it is saturated, can be disabled so that the other receivers can operate normally. In addition, processes can be included in the control circuitry to eliminate multi-path interference when multiple transmitters and/or receivers are employed.

An embodiment of a tattoo system of the present invention can have: a) encoding technology that will not allow external interference (pre-existing wireless machines cannot guarantee this feature), b) a consistent power frequency and/or c) an input voltage that is consistent and not influenced by changes in external power supply.

An embodiment of a tattoo system of the present invention has an option of a new practical and easy to use a clamping mechanism which uses leveraged power to clamp onto the tube and not a thread and screw system that can wear out be constantly be straining on the fingers.

Techniques to reduce power may be incorporated into various embodiments, including using a driver delay and/or relying upon the spring bounce energy.

The driver delay can best be understood by analyzing it as a pendulum or swing movement. For instance, if a person is pushing a regular playground swing and the swing on each cycle is pushed too early during its pendulum swing, the weight and momentum of the swing will exert force to push the person backwards and the person will have to work harder to keep the swing going. However, if the person waits until the swing reaches the full extent of its pendulum swing and then starts to swing back the other way, much less energy is required to keep the swing moving. Similarly, in a typical tattoo gun, the armature swings from a first position downward to a second position and then back. When the armature moves downwardly, the electrical current is removed from the coils. As the armature returns to the first position, the electrical current is again applied to the coils. However, in current tattoo guns, this current is applied too early in the swing cycle and as a result the current flows too early and it counteracts the swinging armature. As such, energy is wasted.

In various embodiments of the present invention, this wasted energy is saved by utilizing a software or circuit induced delay to retard the application of the current to the coils until the armature has traveled its full length to either the first or second position and in essence, has reversed direction similar to a pendulum. This delay can be optimized by the software taking into account the present power setting, the mass of the swinging armature, and the spring constants.

With regards to spring bound, in an ideal swing, there should be as little resistance as possible to minimize the energy loss. If a swinging pendulum hits an object at the end of the arc, energy is typically lost by the impact. If the pendulum hits a spring near the end of its travel distance, the spring would be compressed and absorb the energy and then transfer some (and typically most) of that energy back into swinging the pendulum the other direction. In applying this knowledge to a tattoo gun, the swing of the armature can be optimized to minimize energy loss. Typically, the tattoo gun applies current to the coils to start the armature into a downwardly swing and continues to apply the current until the armature hits the top of the coil core which then becomes a mechanical stop of the armature. At this point, a clicking noise is created from the collision and energy is lost or absorbed into the core. Embodiments of the present invention may utilize a small stiff spring at the end of the armature down stroke. For instance, if a spring 160 is placed between the armature 114 and the coil 118b, then energy is absorbed by the spring during the down stroke of the armature 114. This energy, at some level of loss but much less loss than the striking the core of the coil, is then transferred back into moving the armature 114 in the up swing. The spring 160 can be made of a non-magnetic material so as not to affect the function of the electromagnetic circuit.

FIG. 5 also illustrates a spring holder 506 that can be incorporated into various embodiments of the invention. The illustrated spring holder 506 prevents or limits spring rotation or movement. Generally, tattoo guns, being electro-mechanical devices, operate in a resonant mode and experience considerable vibration. As such, they must often times be adjusted or realigned to maintain accuracy. The adjustments necessary to achieve a desired operating frequency, stroke length, and stroke force can be complex. Many of these adjustments require changing the location of the armature and the support springs. Tightening up the mounting screws 138 and 140 can result in causing the support springs 120 to rotate and the armature 114 to move sideways and thus be out of alignment. It can often take several tries to get the adjustments right and it is difficult to counteract the spring rotation by holding it with fingers while tightening the screw 138.

This spring holder aspect can be incorporated in a tattoo gun by including a square or rectangular support post 502 (shown in FIG. 1) for the spring 126. By making the spring 126 the same width as the support post 502, a non-rotating washer or cap 506 can be placed over the spring 126 with edges descending on both sides of the spring. This assembly operates to lock the spring 126 in a fixed non-rotatable assembly. In another embodiment, rather than using the cap 506 a recess can be formed in the mounting post so that a spring sits in a U-shaped trough or other concave or convex surface (for instance protrusion pins from the surface of the support post 502 may extend through holes in spring 126). In this embodiment, when the spring is held down by the mounting screw, it again cannot rotate.

A similar structure as illustrated in FIGS. 1 and 5 may also be applied in connecting the spring 120 to the armature 114.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A method of controlling a tattoo apparatus wherein the tattoo apparatus comprises a tattoo applicator and a remote control unit, wherein the tattoo applicator comprises:
a wireless receiver to receive wireless signals,
a pen assembly, storage to store a reciprocating frequency for the pen assembly, an armature operatively connected to the pen assembly,
at least one coil configured to attract the armature when the at least one coil is electromagnetic and wherein the remote control unit is physically remote from the tattoo applicator and configured to wirelessly transmit an on signal or off signal to the tattoo applicator when a switch on the remote control unit is actuated, and a circuit compartment having electronics and controls including
a processor,
a micro-controller,
control outputs,
a voltage regulator circuit, and
an interface to the at least one coil for providing or restricting a current from flowing through the at least one coil, the method comprising:
storing in the tattoo applicator a reciprocating frequency for the pen assembly; electronically generating a supply voltage having a frequency based on the reciprocating frequency when an on signal is wirelessly received by the tattoo applicator; and
applying the supply voltage to the at least one coil.

2. The method of claim 1, further comprising:
resetting a timer in the tattoo applicator when an on signal is received from the remote control unit, wherein
the supply voltage is applied to the at least one coil until an off signal is wirelessly received by the tattoo applicator or the timer reaches a predetermined value; and
the remote control unit periodically transmits an on signal to the tattoo applicator once the switch on the remote control unit is actuated to transmit an on signal until the switch is actuated to transmit an off signal.

3. The method of claim 1, further comprising:
computing a time to apply the supply voltage to the at least one coil based on a location of the armature, and
applying the supply voltage to the at least one coil based on the computed time.

4. The method of claim 1, further comprising:
synchronizing the remote control unit to one of a plurality of tattoo applicators in the same vicinity.

5. The method of claim 1, further comprising:
synchronizing a plurality of remote control units in the same vicinity to corresponding tattoo applicators in the same vicinity.

6. A tattoo apparatus comprising:
a tattoo applicator comprising:
a wireless receiver to receive wireless signals;
a pen assembly;
storage to store a reciprocating frequency for the pen assembly;
an armature operatively connected to the pen assembly;
at least one coil configured to attract the armature when the at least one coil is electromagnetic; and
a circuit compartment having electronics and controls including a processor, a micro-controller, control outputs, a voltage regulator circuit, and an interface to the at least one coil for providing or restricting a current from flowing through the at least one coil;
a remote control unit that is physically remote from the tattoo applicator and configured to wirelessly transmit an on or off signal to the tattoo applicator when a switch on the remote control unit is actuated;

wherein the tattoo applicator further comprises a voltage controller configured to generate a supply voltage having a frequency based on the reciprocating frequency when an on signal is wirelessly received by the tattoo applicator and apply the supply voltage to the at least one coil.

7. The tattoo apparatus of claim 6, wherein:

the tattoo applicator further comprises a timer configured to start or restart when an on signal is received from the remote control unit;

the voltage regulator is configured to apply the supply voltage to the at least one coil until an off signal is wirelessly received by the tattoo applicator or the timer reaches a predetermined value; and the remote control unit is configured to periodically transmit an on signal to the tattoo applicator once the switch on the remote control unit is actuated to transmit an on signal until the switch is released or actuated to transmit an off signal.

8. The tattoo apparatus of claim 6, wherein the tattoo applicator further comprises:

computer readable medium comprising a set of instructions which, if executed by a processor, cause the processor to compute a time to apply the supply voltage to the at least one coil based on a location of the armature wherein the voltage regulator is configured to apply the supply voltage to the at least one coil based on the computed time.

9. The tattoo apparatus of claim 6, further comprising:

computer readable medium comprising a set of instructions which, if executed by a processor, cause the processor to synchronize the remote control unit to one of a plurality of tattoo applicators.

10. The tattoo apparatus of claim 6, further comprising:

a spring in between the armature and the top of the at least one coil such that the armature makes contact with the spring when the at least one coil attracts the armature when the at least one coil is electromagnetic.

11. The tattoo apparatus of claim 6, wherein the remote control unit comprises a plurality of transmitters.

* * * * *